United States Patent [19]

Schmidt et al.

[11] Patent Number: 5,717,096
[45] Date of Patent: Feb. 10, 1998

[54] PROCESS FOR THE PREPARATION OF A 2-ALKOXY-6-(TRIFLUOROMETHYL) PYRIMIDIN-4-OL

[75] Inventors: Beat Schmidt, Baltschieder; Gerhard Stucky, Brig-Glis, both of Switzerland

[73] Assignee: Lonza AG, Gampel/Valais, Switzerland

[21] Appl. No.: 823,163

[22] Filed: Mar. 25, 1997

[30] Foreign Application Priority Data

Mar. 26, 1996 [CH] Switzerland .......................... 0780/96
Jul. 11, 1996 [CH] Switzerland .......................... 1740/96

[51] Int. Cl.$^6$ .................................................. C07D 239/52
[52] U.S. Cl. ............................................................. 544/309
[58] Field of Search ..................................... 544/309

[56] References Cited

U.S. PATENT DOCUMENTS

| | | | |
|---|---|---|---|
| 3,580,913 | 5/1971 | Lutz | 544/309 |
| 3,635,977 | 1/1972 | Lutz | 544/309 |
| 3,966,730 | 6/1976 | Hofer et al. | 260/250 |
| 5,352,787 | 10/1994 | Andres et al. | 544/309 |
| 5,463,055 | 10/1995 | Hintermaier et al. | 544/299 |

FOREIGN PATENT DOCUMENTS

| | | |
|---|---|---|
| 0 407 873 | 1/1991 | European Pat. Off. . |
| 0 603 893 | 6/1994 | European Pat. Off. . |
| 0603893 | 6/1994 | European Pat. Off. . |
| 685497 | 7/1995 | Switzerland . |
| 1296371 | 11/1972 | United Kingdom . |

WO 96-16047   5/1996   WIPO .

OTHER PUBLICATIONS

Felczak et al., J. Med. Chem., vol. 39, No. 8, (Apr. 12, 1996), pp. 1720 to 1728.
Botta et al., Tetrahedron, 84, vol. 40, (17), pp. 3313 to 3320 (1984).
Lutz et al., J. Heterocycl. Chem., vol. 9, No. 3, (Jun. 1972), pp. 513 to 522.

*Primary Examiner*—John M. Ford
*Attorney, Agent, or Firm*—Fisher, Christen & Sabol

[57] ABSTRACT

A novel process for the preparation of a 2-alkoxy-6-(trifluoromethyl)pyrimidin-4-ol of the general formula:

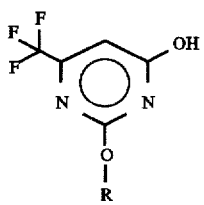

I in which R is a $C_1$–$C_8$-alkyl group. In the process, cyanamide is reacted with the appropriate alcohol in the presence of hydrogen chloride to give the corresponding alkoxyisourea hydrochloride, which is then converted with ethyl trifluoroacetoacetate in the presence of an alkali metal hydroxide, which is in water, to the end product of the formula I.

11 Claims, No Drawings

PROCESS FOR THE PREPARATION OF A 2-ALKOXY-6-(TRIFLUOROMETHYL) PYRIMIDIN-4-OL

BACKGROUND OF THE INVENTION

1. Field Of The Invention

The invention relates to a novel process for the preparation of a 2-alkoxy-6-(trifluoromethyl)pyrimidin-4-ol from cyanamide.

2. Background Art

2-Alkoxy-6-(trifluoromethyl)pyrimidin-4-ols, such as, 2-isopropoxy-6-(trifluoromethyl)pyrimidin-4-ol, are important intermediates for the manufacture of insecticides (European Published Patent Application No. A 0,407,873).

Swiss Patent No. 685,49;7 and European Published Patent Application No. A 0,603,893 disclose the preparation of 2-ethoxy-4,6-dihydroxypyrimidine. Here, cyanamide is converted with ethanol and hydrogen chloride to the corresponding isourea derivative, which is then reacted with diethyl malonate in the presence of sodium ethylate, which is in ethanol, to give the end product. The disadvantages of these processes are, on the one hand, relatively long reaction times and, on the other hand, the fact that the NaCl formed has to be filtered off.

BROAD DESCRIPTION OF THE INVENTION

The main object of the invention is to provide a more economic process for the preparation of a 2-alkoxy-6-(trifluoromethyl)pyrimidin-4-ol which is carried out in a substantially shorter time and without NaCl filtration. Other objects and advantages of the invention are set out herein or are obvious herefrom to one skilled in the art.

The objects of the invention are achieved by the processes of the invention.

The invention involves a process for the preparation of a 2-alkoxy-6-(trifluoromethyl)pyrimidin-4-ol of the general formula:

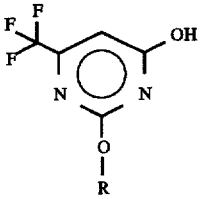

in which R is a $C_1$–$C_8$-alkyl group. The process includes, in the first step, reacting cyanamide with a $C_1$–$C_8$-alcohol in the presence of hydrogen chloride to give the corresponding alkoxyisourea hydrochloride, which, in the second step, is then converted with ethyl trifluoroacetoacetate in the presence of an alkali metal hydroxide, which is in water, to the end product of the formula I.

Preferably the alkali metal hydroxide used is sodium hydroxide. Preferably the alkali metal hydroxide is used in equimolar proportions relative to the ethyl trifluoroacetoacetate. Also, preferably the first step of the reaction is carried out at a temperature of 50° to 70° C. Preferably the second step of the reaction is carried out at a temperature of 85° to 95° C. Preferably the reaction is carried out without isolation of the alkoxyisourea hydrochloride.

The invention also involves a second process for the preparation of a 2-alkoxy-6-(trifluoromethyl)pyrimidin-4-ol of the general formula:

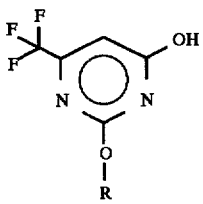

in which R is a $C_1$–$C_8$alkyl group. The process includes reacting the appropriate alkoxyisourea hydrochloride with ethyl trifluoroacetoacetate in the presence of an alkali metal hydroxide, which is in water.

DETAILED DESCRIPTION OF THE INVENTION

According to the invention, the process is carried out in such a way that, in the first step, cyanamide is reacted with a $C_1$–$C_8$-alcohol in the presence of hydrogen chloride to give the corresponding alkoxyisourea hydrochloride, which, in the second step, is then reacted with ethyl trifluoroacetoacetate in the presence of an alkali metal hydroxide, which is in water, to give the end product of the general formula:

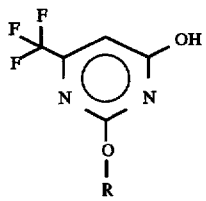

in which R is a $C_1$–$C_8$-alkyl group. Examples of R are methyl, ethyl, propyl, i-propyl, butyl, i-butyl, pentyls, hexyls, heptyls and octyls. R is preferably i-propyl, propyl or i-butyl.

The alkali metal hydroxide used can be sodium or potassium hydroxide, preferably sodium hydroxide. The alkali metal hydroxide is preferably used in equimolar proportions relative to the ethyl trifluoroacetoacetate.

Methanol, ethanol, propanol, i-propanol, butanol, i-butanol, pentanols, hexanols, heptanols or octanols can be used as the $C_1$–$C_8$-alcohol. It is preferable to use i-propanol, propanol or i-butanol.

The first step of the reaction is conveniently carried out at a temperature of 0° to 100° C., and preferably at a temperature of 50° to 70° C. The second step is conveniently carried out at a temperature of 50° to 100° C., and preferably of 85° to 95° C.

The reaction can be carried out either with or without isolation of the appropriate alkoxyisourea hydrochloride. The reaction is preferably carried out without isolation of the alkoxyisourea hydrochloride.

The total reaction time is between 6 and 8 hours. The NaCl formed during the reaction is dissolved in water and, therefore, there is no need to filter off the formed NaCl.

EXAMPLE 1

Preparation of 2-isopropoxy-6-(trifluoromethyl)pyrimidin-4-ol 11.25 g (263 mmol; 1.05 eq) of cyanamide was placed is isopropanol (800 ml per tool of ethyl trifluoroacetoacetate; EtTFAA) at 50° C. and HCl gas (18.3 g; 500 mmol; 2.0 eq) was passed through the mixture for one hour. When the introduction of HCl had ended, the mixture was stirred for

EXAMPLE 1

2 hours at 70° C. It was then allowed to cool to room temperature and ¾ of the solvent was evaporated off on a rotary evaporator. 80 ml of water (320 ml per mol of ethyl trifluoroacetoacetate) was added at room temperature to the O-isopropylisourea hydrochloride formed. Aqueous NaOH solution (78.87 g; 1.09 eq; 14 percent according to titration) was then added over 5 minutes at room temperature until the pH had shifted from 0.5 to 11.5, and stirring was continued for 15 minutes. The temperature was kept at ≦30° C. during the addition of the NaOH. Ethyl trifluoroacetoacetate (46.5 g; 500 mmol; 1.0 eq) was then added dropwise to this solution at room temperature. The temperature rose to 30° C. during this process and two phases formed. This mixture was refluxed for 2 hours. The organic solvents were then distilled off until the top temperature reached ca. 96° C. Stirring was continued for 2 hours at 85° to 90° C. The light yellow emulsion was allowed to cool to room temperature, the pH of 7.3 was adjusted to 5.0 with a small amount of 2 N aqueous HCl solution and the granular solid was filtered off after 20 minutes at room temperature. The moist solid obtained after filtration was taken up again with distilled water (~1 g moist product/ml water) and refluxed for 1 hour. After cooling to room temperature, filtration and drying, a light yellowish solid of relatively high content was obtained: the total yield was 67.8 percent (content: 98.0 percent according to HPLC). The solid was washed with a small amount of cold water and then dried overnight in a vacuum drying cabinet at 40° C. 41.3 g of a yellowish solid was obtained as the product, corresponding to a yield of 69.8 percent (content: 94.5 percent according to HPLC).

EXAMPLE 2

Preparation of 2-propoxy-6-(trifluoromethyl)pyrimidin-4-ol 1.05 eq of cyanamide was placed in propanol (800 ml per mol of EtTFAA) at 50° C. and 2.0 eq of HCl gas was passed through the mixture for 0.5 hour (exothermic, gentle water cooling). The solution was then heated to 70° C. and kept at this temperature for 2 hours. It was then allowed to cool to room temperature and ⅔ of the solvent was evaporated off on a rotary evaporator. 32 ml of water (320 ml per mol of EtTFAA) was added to the O-propylisourea hydrochloride at room temperature. Aqueous NaOH solution (14 percent according to titration) was then added over 7 minutes at room temperature until the pH had shifted from 0 to 11.5 (temp. ≦30° C.; corresponds to 1.1 eq of NaOH), and stirring was continued for 15 minutes. 1.0 eq of EtTFAA was then added dropwise to this solution over 2 minutes. The temperature rose to 32° C. during this process and two phases formed. This mixture was refluxed (~88° C.) for two hours. The organic solvents were then distilled off until the top temperature reached ~95 ° C. Stirring was continued for 2 hours at 84° to 85° C. The light yellow emulsion was allowed to cool to room temperature and the pH was adjusted to 5.0 with a small amount of concentrated HCl solution. The suspension was cooled to 4° C. overnight. The granular solid was filtered off, washed with a small amount of cold water and then dried overnight in a vacuum drying cabinet at 40° C. The yield of the product was 13.1 g of a sticky solid; 52.36 percent (content: 88.8 percent according to GC area percent). Other data concerning the product was:

$^1$H NMR:

1.0 (t, 3 H, $CH_3$),
1.8 (m, 2 H, $CH_2$),
4.4 (m, 2 H, $CH_2$),
6.5 (s, 1 H, ar-H),
12 (s, 1 H, OH).

EXAMPLE 3

Preparation of 2-isobutoxy-6-(trifluoromethyl)pyrimidin-4-ol 1.05 eq of cyanamide was placed in isobutanol (800 ml per mol of EtTFAA) at 50° C. and 2.0 eq of HCl gas was passed through the mixture for 0.5 hour (exothermic, gentle water cooling). The solution was then heated to 70° C. and kept at this temperature for 2 hours. It was then allowed to cool to room temperature and the solvent was evaporated off on a rotary evaporator. 32 ml of water (320 ml per mol of EtTFAA) was added to the O-isobutylisourea hydrochloride at room temperature. Aqueous NaOH solution (14 percent according to titration) was then added over 9 minutes at room temperature until the pH had shifted from 0 to 11.5 (temperature ≦30° C.; corresponds to 1.8 eq of NaOH), and stirring was continued for 15 minutes. 1.0 eq of EtTFAA was then added dropwise to this solution over 2 minutes. The temperature rose to 30° C. during this process and two phases formed. This mixture was refluxed (~90° C. to 92° C.) for 2 hours. The organic solvents were then distilled off until the top temperature reached ~93° C. Stirring was continued for 2 hours at 85° to 86° C. The light yellow emulsion was allowed to cool to room temperature and the pH of 8.5 was adjusted to 5.0 with a small amount of concentrated HCl solution. The suspension was left to stand overnight at 4° C. The granular solid was filtered off, washed with a small amount of cold water and then dried overnight in a vacuum drying cabinet at 40° C. The yield of the product was 14.09 g of a yellow oil; 59.6 percent (content: 85.3 percent according to GC area percent). Other data concerning the product was:

$^1$H NMR:

1.0 (d, 6 H, $CH_3$),
2.1 (m, 2 H, CH),
4.2 (d, 2 H, $CH_2$),
6.5 (s, 1 H, ar-H),
2 (s, 1 H, OH).

What is claimed is:

1. A process for the preparation of a 2-alkoxy-6-(trifluoromethyl)pyrimidin-4-ol of formula:

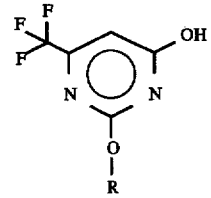

wherein R is a $C_1$–$C_8$-alkyl group, comprising, in a first step, reacting cyanamide with a $C_1$–$C_8$-alcohol in the presence of hydrogen chloride to give the corresponding alkoxyisourea hydrochloride, and, in a second step, then converting the corresponding alkoxyisourea hydrochloride with ethyl trifluoroacetoacetate in the presence of an alkali metal hydroxide, which is in water, to the 2-alkoxy-6-(trifluoromethyl)pyrimidin-4-ol of formula I.

2. The process according to claim 1, wherein the alkali metal hydroxide used is sodium hydroxide.

3. The process according to claim 1, wherein the alkali metal hydroxide is used in equimolar proportions relative to the ethyl trifluoroacetoacetate.

4. The process according to claim 3, wherein the first step of the reaction is carried out at a temperature of 0° to 100° C.

5. .The process according to claim 3, wherein the second step of the reaction is carried out at a temperature of 50° to 100° C.

6. The process according to claim 5, wherein the reaction in the second step is carried out without isolation of the alkoxyisourea hydrochloride from the first step.

7. The process according to claim 6, wherein the reaction in the second step is carried out without isolation of the alkoxyisourea hydrochloride from the first step.

8. The process according to claim 1, wherein the first step of the reaction is carried out at a temperature of 0° to 100° C.

9. The process according to claim 1, wherein the second step of the reaction is carried out at a temperature of 50° to 100° C.

10. The process according to claim 1, wherein the reaction in the second step is carried out without isolation of the alkoxyisourea hydrochloride from the first step.

11. A process for the preparation of a 2-alkoxy-6-(trifluoromethyl)pyrimidin-4-ol of formula:

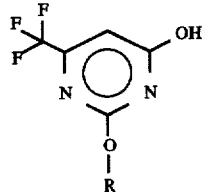

wherein R is a $C_1$–$C_8$-alkyl group, comprising reacting the corresponding alkoxyisourea hydrochloride with ethyl trifluoroacetoacetate in the presence of an alkali metal hydroxide, which is in water.

* * * * *